(12) United States Patent
DeLong Samalik et al.

(10) Patent No.: US 11,832,984 B2
(45) Date of Patent: Dec. 5, 2023

(54) SYSTEM AND METHOD FOR MOTION GUIDANCE DURING MEDICAL IMAGE ACQUISITION

(71) Applicant: GE Precision Healthcare LLC, Wauwatosa, WI (US)

(72) Inventors: Michelle Marie Severino DeLong Samalik, Milwaukee, WI (US); Chelsey A. Lewis, Milwaukee, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 161 days.

(21) Appl. No.: 17/212,385

(22) Filed: Mar. 25, 2021

(65) Prior Publication Data

US 2022/0304645 A1 Sep. 29, 2022

(51) Int. Cl.
| A61B 6/00 | (2006.01) |
| G06T 7/20 | (2017.01) |
| G06T 7/70 | (2017.01) |
| G08B 7/06 | (2006.01) |
| A61B 6/03 | (2006.01) |
| G16H 30/40 | (2018.01) |
| G16H 40/67 | (2018.01) |

(52) U.S. Cl.
CPC ............. *A61B 6/527* (2013.01); *A61B 6/035* (2013.01); *A61B 6/461* (2013.01); *A61B 6/54* (2013.01); *G06T 7/20* (2013.01); *G06T 7/70* (2017.01); *G08B 7/06* (2013.01); *G16H 30/40* (2018.01); *G16H 40/67* (2018.01); *G06T 2207/30196* (2013.01)

(58) Field of Classification Search
CPC ......... A61B 6/527; A61B 6/035; A61B 6/461; A61B 6/54; A61B 6/032; G06T 7/20; G06T 7/70; G06T 2207/30196; G08B 7/06; G16H 30/40; G16H 40/67
See application file for complete search history.

(56) References Cited

U.S. PATENT DOCUMENTS

| 76,780,632 | | 7/2007 | Felmlee | |
| 2019/0228866 A1* | | 7/2019 | Weffers-Albu | G16H 40/63 |
| 2020/0258243 A1* | | 8/2020 | Chang | A61B 5/107 |

FOREIGN PATENT DOCUMENTS

EP 30739171 A 10/2016

\* cited by examiner

*Primary Examiner* — Nam D Pham

(57) ABSTRACT

The present disclosure relates to systems and methods for monitoring and guiding patient motion during medical image acquisition. In accordance with certain embodiments, a method includes acquiring an image of a patient with an imaging system; determining an amount of patient movement; and providing a movement indicator based on the determined amount of patient movement.

19 Claims, 7 Drawing Sheets

SYSTEM AND METHOD FOR MOTION GUIDANCE DURING MEDICAL IMAGE ACQUISITION

TECHNICAL FIELD

This disclosure relates to monitoring and guiding patient motion during a medical image acquisition and, more particularly, to monitoring and guiding patient motion during computed tomography (CT) imaging.

BACKGROUND

Non-invasive imaging technologies allow images of the internal structures of a patient to be obtained without performing an invasive procedure on the patient. In particular, technologies such as computed tomography (CT) use various physical principles, such as the differential transmission of X-rays through a target volume (i.e., a patient being imaged), to acquire image data and to construct tomographic images (i.e., three-dimensional representations of the interior of the human body).

A CT scanner includes an X-ray source mounted on a rotatable gantry that rotates around an examination region. The X-ray source emits radiation that traverses the examination region and a patient positioned therein. An X-ray sensitive radiation detector array subtends an angular arc opposite the examination region from the X-ray source detects radiation that traverses the examination region and generates a signal indicative thereof. A reconstructor processes the signal and reconstructs image data indicative of a portion of the patient.

During image acquisition it is vital that a patient remain motionless as voluntary or involuntary patient movement may cause a motion artifact to appear in the reconstructed image. Motion artifacts may appear as blurring, streaking, or shading which may render the reconstructed image unusable for diagnostic purposes. As a result, the patient may have to undergo a second imaging procedure wherein the patient is subjected to additional radiation. If the patient continues to move, the patient may be immobilized or sedated in order to ensure a useable image may be acquired.

SUMMARY

In one aspect, the present disclosure provides a method. The method includes acquiring an image of a patient with an imaging system, determining an amount of patient movement, and providing a movement indicator based on the determined amount of patient movement.

In another aspect, the present disclosure provides a system. The system includes an imaging system configured to acquire at least one image of a patient, at least one camera configured to acquire a plurality of optical images of an outer region of interest (ROI) of the patient, at least one processor, and at least one computer readable storage medium in communication with the at least one processor. The at least one processor executes computer readable instructions stored in the at least one computer readable storage medium which cause the at least one processor to determine an amount of patient movement, and provide a movement indicator based on the amount of patient movement.

In yet another aspect, the present disclosure provides a computer readable storage medium with computer readable program instructions. When the computer readable program instructions are executed by the processor, they cause the processor to determine an amount of patient movement by comparing a position of the patient in a first optical image to a position of the patient in a second optical image, and provide a movement indicator based on the amount of patient movement, wherein the movement indicator is a light or a prerecorded audio message.

BRIEF DESCRIPTION OF THE DRAWINGS

Various aspects of this disclosure may be better understood upon reading the following detailed description with reference to the drawings in which.

Figure 1:
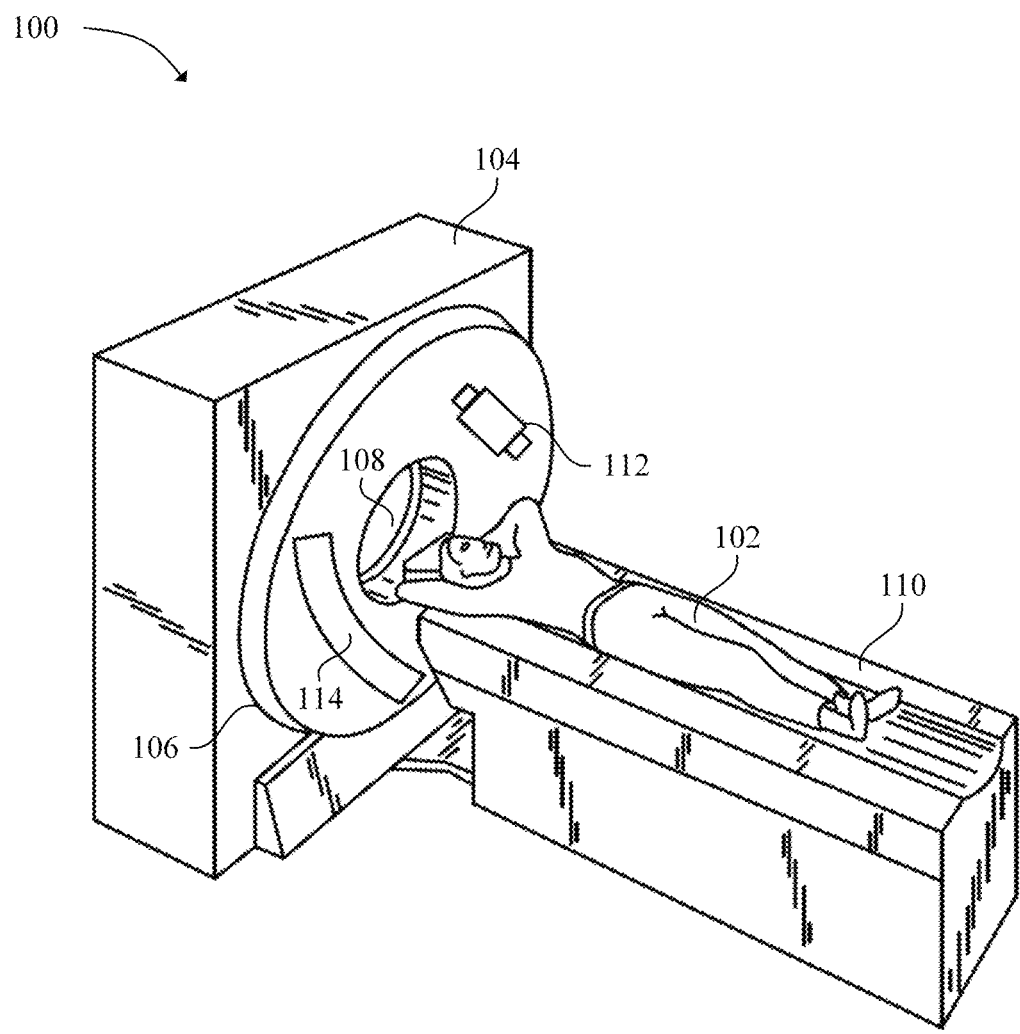
FIG. 1 depicts a CT imaging system in accordance with an exemplary embodiment.

The drawings illustrate specific acts of the described components, systems, and methods for monitoring and guiding patient motion during a medical image acquisition. Together with the following description, the drawings demonstrate and explain the structures, methods, and principles described herein. In the drawings, the thickness and size of components may be exaggerated or otherwise modified for clarity. Well-known structures, materials, or operations are not shown or described in detail to avoid obscuring aspects of the described components, systems, and methods.

DETAILED DESCRIPTION

One or more specific embodiments of the present disclosure are described below. These described embodiments are only examples of the systems and methods for monitoring and guiding patient motion during a medical image acquisition. The skilled artisan will understand that specific details described in the embodiments can be modified when being placed into practice without deviating from the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (i.e., a material, element, structure, number, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In order to avoid motion artifacts in a reconstructed image, patients are told to remain still during image acquisition, but are provided no feedback during acquisition as to if they are holding still. Anxiety and nervousness of the patient, which may cause the patient to move, may be calmed by providing a feedback mechanism to the patient that they are remaining motionless during image acquisition. Some embodiments of the present disclosure provide systems/methods that include using a camera to detect patient movement and then the system providing a visual or audio indicator to the patient and a technologist or operator operating the CT scanner during image acquisition to indicate patient movement beyond a movement threshold. Providing a system/method that provides a feedback mechanism to the patient and CT scanner technologist (operator) that may indicate patient movement. Such feedback mechanism may reduce patient movement during image acquisition thereby reducing motion artifacts in a reconstructed image.

Furthermore, if a patient does move during image acquisition and such movement may render the image unusable for diagnostic purposes, a technician may stop image acquisition in order to reduce the amount of patient radiation exposure. Such movement may be missed by the technician causing the patient to unnecessarily be exposed to additional radiation. Some embodiments of the present disclosure include systems/methods that detect patient movement and automatically abort image acquisition. Other embodiments of the present disclosure provide systems/methods that notify the technician that the patient has moved.

Referring to the figures generally, the present disclosure describes systems and methods for monitoring and guiding patient motion during a medical image acquisition.

While the following describes a system and method for monitoring or guiding patient movement while undergoing a CT scan, it is understood that present techniques may also be useful when applied to other imaging systems, such as an X-ray imaging system, a magnetic resonance (MR) imaging system, a positron emission tomography (PET) imaging system, single-photon emission computed tomography (SPECT) imaging system, an ultrasound imaging system, a fluoroscopic X-ray imaging system, and combinations thereof (i.e., multi-modality imaging systems, such as PET/CT, PET/MR or SPECT/CT imaging systems). The present discussion of a CT imaging system is provided merely as an example of one suitable imaging system.

Referring now to FIG. 1, a CT imaging system 100 that is configured to image a patient 102 is shown in accordance with an exemplary embodiment. As illustrated in FIG. 1, in some embodiments, the CT imaging system 100 includes an enclosure 104 and rotating gantry 106. The rotating gantry 106 which rotates about an examination region 108. The CT imaging system 100 also includes a patient support (i.e., couch, table, etc.) 110. The patient support 110 supports the patient 102 while at least a portion of the patient 102 is within the examination region 108. The CT imaging system 100 further includes an X-ray source 112 and an X-ray detector array 114. The X-ray source 112 and the X-ray detector array 114 are supported by and rotate with the rotating gantry 106. Although FIG. 1 depicts only a single X-ray source 112, in other embodiments, the CT imaging system 100 may include multiple X-ray sources 112.

Figure 2:
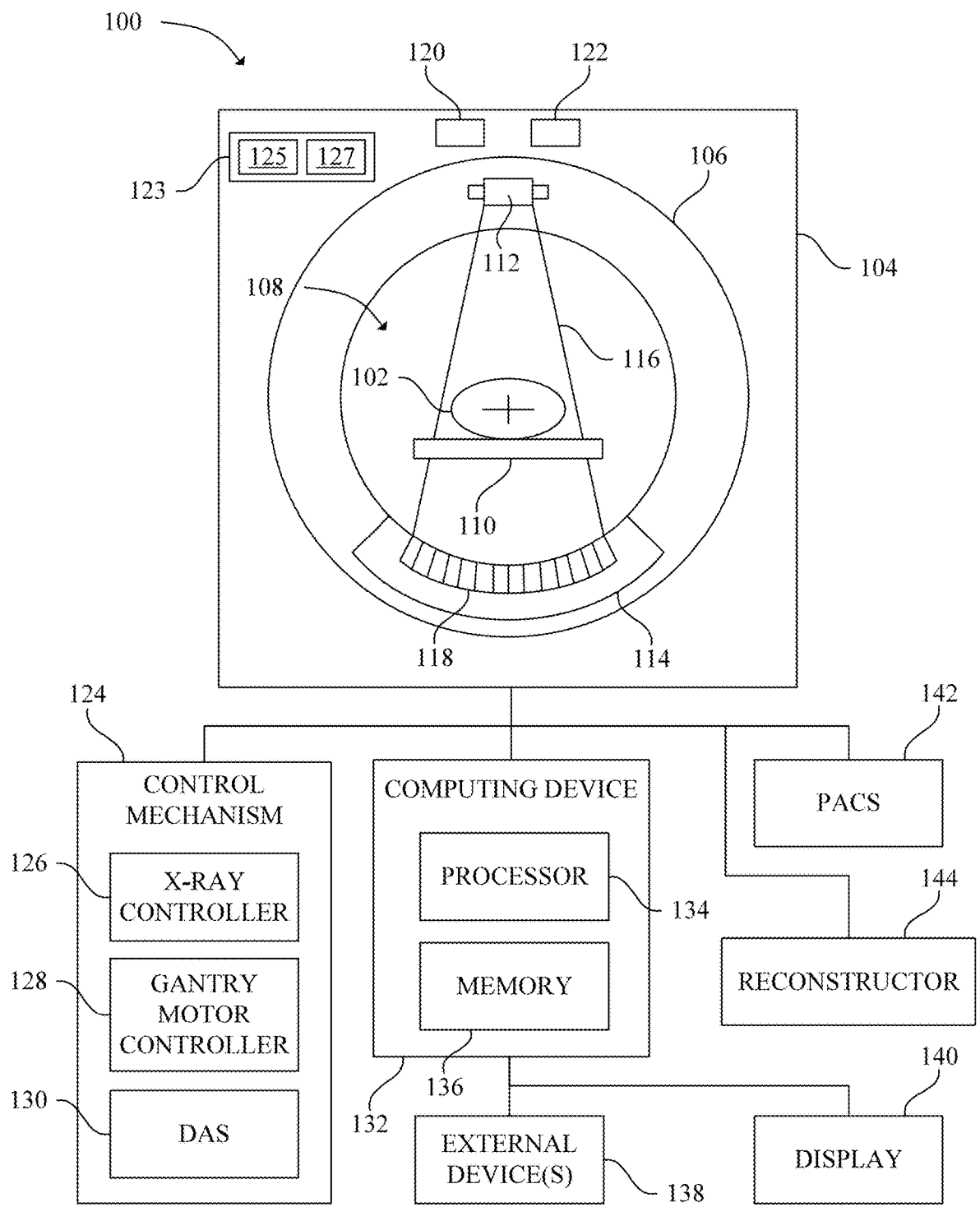
FIG. 2 is a block diagram of the CT imaging system depicted in FIG. 1 in accordance with an exemplary embodiment.

Briefly turning to FIG. 2, a block diagram of the CT imaging system 100 is shown in accordance with an exemplary embodiment. As shown in FIG. 2, the X-ray source 112 emits X-ray radiation in the form of an X-ray beam 116. The X-ray beam 116 traverses the examination region 108 and is attenuated by the patient 102. Specifically, the X-ray source 112 emits the radiation-ray beam 116 towards the X-ray detector array 114 which is positioned directly opposite from the X-ray source 112 on the rotating gantry 106. In some embodiments, the X-ray source 112 emits a cone-shaped X-ray beam 116 which is collimated to lie with an X-Y-Z plane of a Cartesian coordinate system which is generally referred to as an "imaging plane."

The X-ray detector array 114 includes a plurality of detector elements 118. The detector elements 118 detect the attenuated radiation that passes through the patient 102 to acquire corresponding projection data. Each detector element of the X-ray detector array 114 produces an electrical signal that is a measurement of the attenuation at the detector element 118 location. The attenuation measurements from all the detector elements 118 are acquired to produce a transmission profile. In one embodiment, the X-ray detector array 114 may be fabricated in a multi-slice configuration including a plurality of rows of detector elements 118.

In an exemplary embodiment, the X-ray detector array 114 may be a photon-counting X-ray detector array 114 which is capable of differentiating X-ray photons of different energies. When the X-ray detector array 114 is a photon-counting detector array 114, the X-ray detector elements 118 register the interactions of individual photons into one or more energy bins. It is further appreciated that the X-ray detector elements 118 may also include energy-integrating detector elements 118.

When the X-ray source 112 and the X-ray detector array 114 are rotated with the rotating gantry 106 within the imaging plane and around the patient 102, the angle at which the X-ray beam 116 intersects the patient 102 changes. A group of radiation attenuation measurements (i.e., projection data) from the X-ray detector array 114 at one gantry angle is referred to as a "view." A "scan" of the patient 102 includes a set of views made at different angles, or view angles, during at least one revolution of the X-ray source 112 and the X-ray detector array 114. As used herein, the term "view" is not limited to the use described herein with respect to projection data from one gantry angle. The term "view" is used to mean one data acquisition whenever there are multiple acquisitions from different angles, whether from the CT imaging system 100 or another type of imaging system. To reduce the total scan time, a "helical" scan may be performed. A helical scan is performed by moving the patient support 110 with the patient 102 through the examination region 108 while data for a prescribed number of slices is acquired. A "slice" is used to mean image data acquired in the imaging plane. Such an image acquisition generates a single helix from a single cone beam helical scan. The helix mapped out by the cone beam yields projection data from which images in each prescribed slice may be reconstructed.

As shown in FIG. 2, The CT imaging system 100 further includes a camera 120, at least one light (i.e., fluorescent, incandescent, light-emitting diode (LED), etc.) 122, and an intercom system 123. The camera 120 is supported by the enclosure 104 and captures an optical image of the patient 102 before/while the CT imaging system 100 acquires a medical image of the patient 102. While FIG. 1 depicts the camera 120 as supported by the enclosure 104, in other embodiments, the camera 120 may be located elsewhere in an examination room with the CT imaging system 100 (i.e., on a ceiling, on a wall, etc.). As used herein an optical image includes, but is not limited to, an outer region of interest (i.e., arm, torso, head, etc.) of the patient 102. Furthermore, as used herein, a medical image includes, but is not limited to, an internal structure(s) (or an internal region of interest) (i.e., organ, bone, tissue, blood vessel, etc.) of the patient 102. As such, the camera 120 is positioned such that the view of the camera 120 captures at least an external portion (or region of interest) of the patient 102 while at least a portion of the patient 102 is within the examination region 108. Stated another way, the camera 120 has a field of view (FOV) that includes at least a portion of the examination region and at least a portion of the patient 102 when the patient 102 is being imaged. In some embodiments, the camera 120 is a video camera 120. In these embodiments, the camera 120 sequentially captures a plurality of images in real-time. As will be discussed in further detail herein, the optical images captured by the camera 120 are processed to determine if the patient 102 is moving during a medical image acquisition. Furthermore, as used herein, a medical image acquisition period includes, but is not limited to, a period of time when the X-ray source 112 is emitting radiation.

Figure 3:
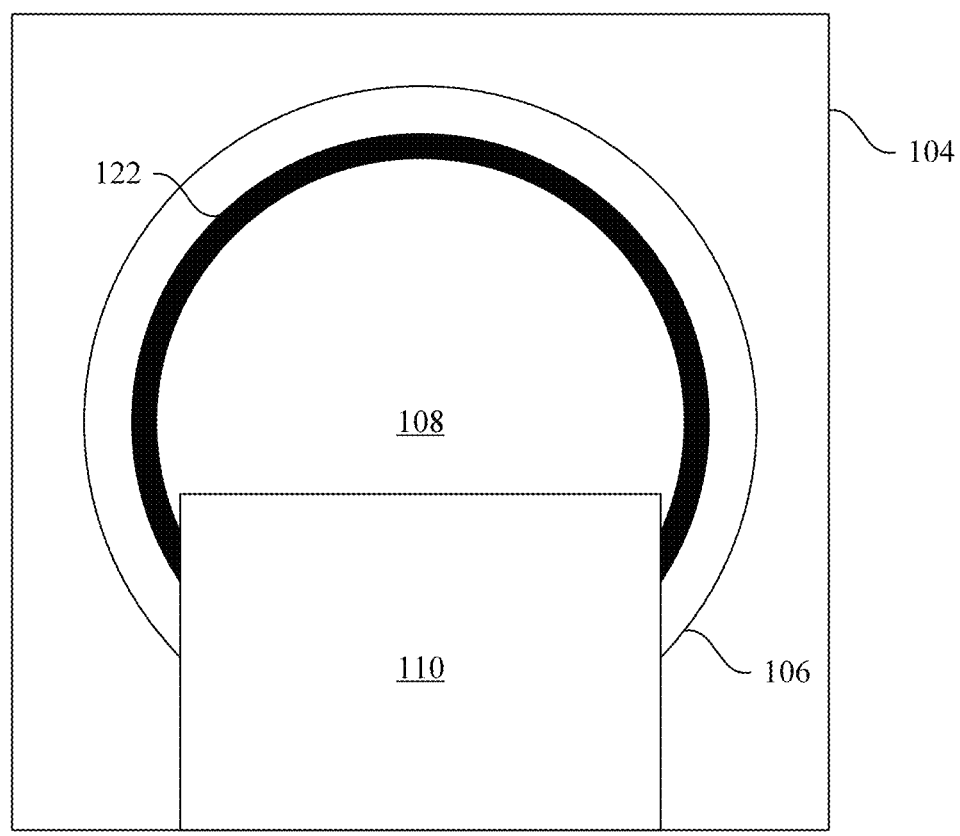
FIG. 3 depicts a front view of the CT imaging system depicted in FIG. 1 in accordance with an exemplary embodiment.

In some embodiments, the light 122 is supported by the enclosure 104. While FIG. 2 depicts the light 122 as supported by the enclosure 104, in other embodiments the light 122 is supported by the rotating gantry 106. The light 122 is positioned such the patient 102 may view light that is emitted by the light 122 as the patient 102 is being imaged. In some embodiments, the light 122 is configured to emit different colored light (i.e., red, green, yellow, etc.). Stated another way, the light 122 is positioned such that the light 122 emits light into the examination region 108. As will be discussed in further detail herein, in these embodiments, the light 122 emits light in response to determining if the patient is moving or stationary during a medical image acquisition in the images captured by the camera 120. Briefly turning to FIG. 3, a front view of the CT imaging system 100 is shown in accordance with an exemplary embodiment. In this embodiment, the light 122 subtends an angular arch about the examination region 108.

The intercom system 123 may be supported by the enclosure 104. While FIG. 2 depicts the intercom system 123 as supported by the enclosure 104, in some embodiments, the intercom system 123 may be supported by the rotating gantry 106. The intercom system 123 includes a microphone 125 and a speaker 127. The microphone 125 and the speaker 127 allow the patient 102 to communicate with a technician operating the CT system 100. In some embodiments, the speaker 127 plays prerecorded messages to the patient 102.

While FIG. 2 depicts the camera 120, the light 122, and the enclosure 104, in some embodiments, the camera 120, the light 122, and the intercom 123 may be separate from the enclosure 104 and may be located elsewhere within a room containing the CT system 100. For example, the light 122 may be positioned anywhere in a room containing the CT system 100 so long as light emitted by the light 122 is visible to the patient 102 while the patient 102 is being imaged.

The CT imaging system 100 further includes a control mechanism 124. The control mechanism 124 controls rotation of the rotating gantry 106 and operation of the X-ray source 112. In some embodiments, the control mechanism 124 includes an X-ray controller 126 and a gantry motor controller 128. The X-ray controller 126 is configured to provide power and timing signals to the X-ray source 112. The gantry motor controller 128 is configured to control a rotational speed and/or position of the rotating gantry 106 based on imaging requirements. The control mechanism 124 further includes a data acquisition system (DAS) 130. The DAS 130 is configured to sample analog data received from the detector elements 118 and convert the analog data to digital signals for subsequent processing. The DAS 130 may be further configured to selectively aggregate analog data from a subset of the detector elements 118 into macro-detectors.

The CT imaging system 100 further includes a computing device 132. As used herein, a computing device (or system) is any device/system capable of processing and transmitting data (i.e., tablet, handled device, smart phone, personal computer, laptop, network computer, server, mobile communication device, server, etc.). The computing device 132 may be connected to a network (i.e., a wide area network (WAN), a local area network (LAN), a public network (the Internet), etc.) which allows the computing device 132 to communicate with other devices on a same network. In some embodiments, the network may be regarded as a private network connection and may include, for example, a virtual private network or an encryption or other security mechanism employed over the public Internet.

The computing device 132 includes a processor 134 and a system memory 136. In some embodiments, the computing device is connected to one or more external devices 138 and a display 140. The processor 134 is in communication with the system memory 136 and may execute computer readable program instructions stored in the system memory 136. As used herein, a processor may include a central processing unit (CPU), or other electronic components capable of executing computer readable program instructions (i.e., a digital signal processor, a field-programmable gate array (FPGA), or a graphics board and may be configured as a graphical processing unit with parallel processing capabilities). Furthermore, as used herein, a processor may include two or more of a CPU, a digital signal processor, an FPGA, and a graphics board.

The system memory 136 is a computer readable storage medium. As used herein, a computer readable storage medium, such as a non-transitory computer readable storage medium, is any device that stores computer readable program instructions for execution by a processor and is not construed as being transitory per se. Computer readable program instructions include programs, logic, data structures, modules, etc. that when executed by a processor create a means for implementing functions/acts. Computer readable program instructions when stored in a computer readable storage medium and executed by a processor direct a computer system and/or another device to function in a particular manner such that a computer readable storage medium comprises an article of manufacture. System memory as used herein includes volatile memory (i.e., random access memory (RAM) and dynamic RAM (DRAM)) and nonvolatile memory (i.e., flash memory, read-only memory (ROM), magnetic computer storage devices, etc.). In some embodiments, the system memory may further include cache.

In one embodiment, various methods and processes (i.e., the methods described below with reference to FIGS. 5 and 7) may be stored as computer readable program instructions in the system memory 136. In this embodiment, the system memory 136 includes computer readable program instructions for monitoring and guiding patient motion during a medical image acquisition.

The external devices 138 include devices that allow a user to interact with/operate the computing device 132 (i.e., mouse, keyboard, touchscreen, speakers etc.). In some embodiments, the display 140 displays a graphical user interface (GUI). The GUI includes editable fields for inputting data, including, but not limited to, patient information and further includes selectable icons. Selecting an icon or inputting data causes the processor 134 to execute computer readable program instructions stored in the system memory 136 which cause the processor to perform a task. For example, a user of the computing device 132 may use an external device 138 to select a "start icon" or the like which causes the processor 134 to begin an imaging procedure.

The computing device 132 is in communication with and provides commands to the X-ray controller 126, the gantry motor controller, and/or the DAS 130 for controlling system operations such as data acquisition and/or processing. In some embodiments, the computing device 132 controls operation of the X-ray controller 126, the gantry motor controller, and/or the DAS 130 based on a user input.

Although FIG. 2 illustrates only computing device 132, the CT imaging system 100 may include more than one computing device 132, for example, for inputting or outputting system parameters, requesting examinations, plotting data, and/or viewing images. Furthermore, in certain embodiments, the CT imaging system 100 may be coupled to multiple displays, printers, workstations, and/or similar devices located either locally or remotely, for example, within an institution or hospital, or in an entirely different location via one or more configurable wired and/or wireless networks.

In one embodiment, the CT imaging system 100 either includes, or is coupled to, a picture archiving and communications system (PACS) 142. In an exemplary implementation, the PACS 142 is further coupled to a remote system such as a radiology department information system, hospital information system, and/or to an internal or external network (not shown) to allow operators at different locations to supply commands and parameters and/or gain access to the image data.

The CT imaging system 100 further includes or is coupled to an image reconstructor 144. As previously noted, the DAS 130 samples and digitizes the projection data acquired by the detector elements 118. Subsequently, the image reconstructor 144 uses the sampled and digitized X-ray data to perform high-speed reconstruction.

Although FIG. 2 illustrates the image reconstructor 144 as a separate entity, in certain embodiments, the image reconstructor 144 may form part of the computing device 132. Alternatively, the image reconstructor 144 may be absent from the CT imaging system 100 and instead the computing device 132 may perform one or more functions of the image reconstructor 144. Moreover, the image reconstructor 144 may be located locally or remotely and may be operatively connected to the CT imaging system 100 using a wired or wireless network. Particularly, one exemplary embodiment may use computing resources in a "cloud" network environment for the image reconstructor 144.

The reconstructor 144 receives projection data. The projection data undergoes pre-processing and calibration to condition the data to represent the line integrals of attenuation coefficients of the patient 102. The processed data is commonly referred to as "projections." The acquired sets of projection data may be used for basis material decomposition (BMD). During BMD, the measured projections are converted to a set of material-density projections. The material-density projections may be reconstrued to form a pair or a set of material-density map or image of each respective basis material, such as bone, soft tissue, and/or contrast agent maps. The density maps or images may be, in turn, associated to form a volume rendering of the basis material (i.e., bone, soft tissue, and/or contrast agent) in the imaged volume.

The projection data is processed to reconstruct an image that corresponds to a two-dimensional slice taken through the object, or in some examples where the projection data includes multiple views or scans, a three-dimensional rendering of the patient 102. One method for reconstructing an image from a set of projection data is referred to as a "filtered back projection" technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel of a display.

Once reconstructed, a basis material image reveals internal features of the patient 102 expressed in the densities of two basis materials. The image may be displayed to show these features. Once displayed, a practitioner may view the image to make a medical diagnosis or to discern characteristics of a feature of interest (i.e., lesions, anatomies, organs, etc.).

As used herein, the phrase "reconstructing an image" is not intended to exclude embodiments in which data representing an image is generated, but a viewable image is not. Therefore, as used herein, the term image broadly refers to both viewable images and data representing a viewable image. However, some embodiments described herein generate (or are configured to generate) at least one viewable image.

In one embodiment, the reconstructor 144 stores reconstructed images in the system memory 136. In another embodiment, the reconstructor 144 transmits the reconstructed images to the computing device 132 for generating useful patient information for diagnosis and evaluation. In certain embodiments, the computing device 132 may transmit the reconstructed images and/or the patient information to the display 140 and/or the image reconstructor 144. In other embodiments, the reconstructed images may be transmitted from to the system memory 136 or from the reconstructor 144 to the PACS 142 for short-term or long-term storage.

Figure 4:
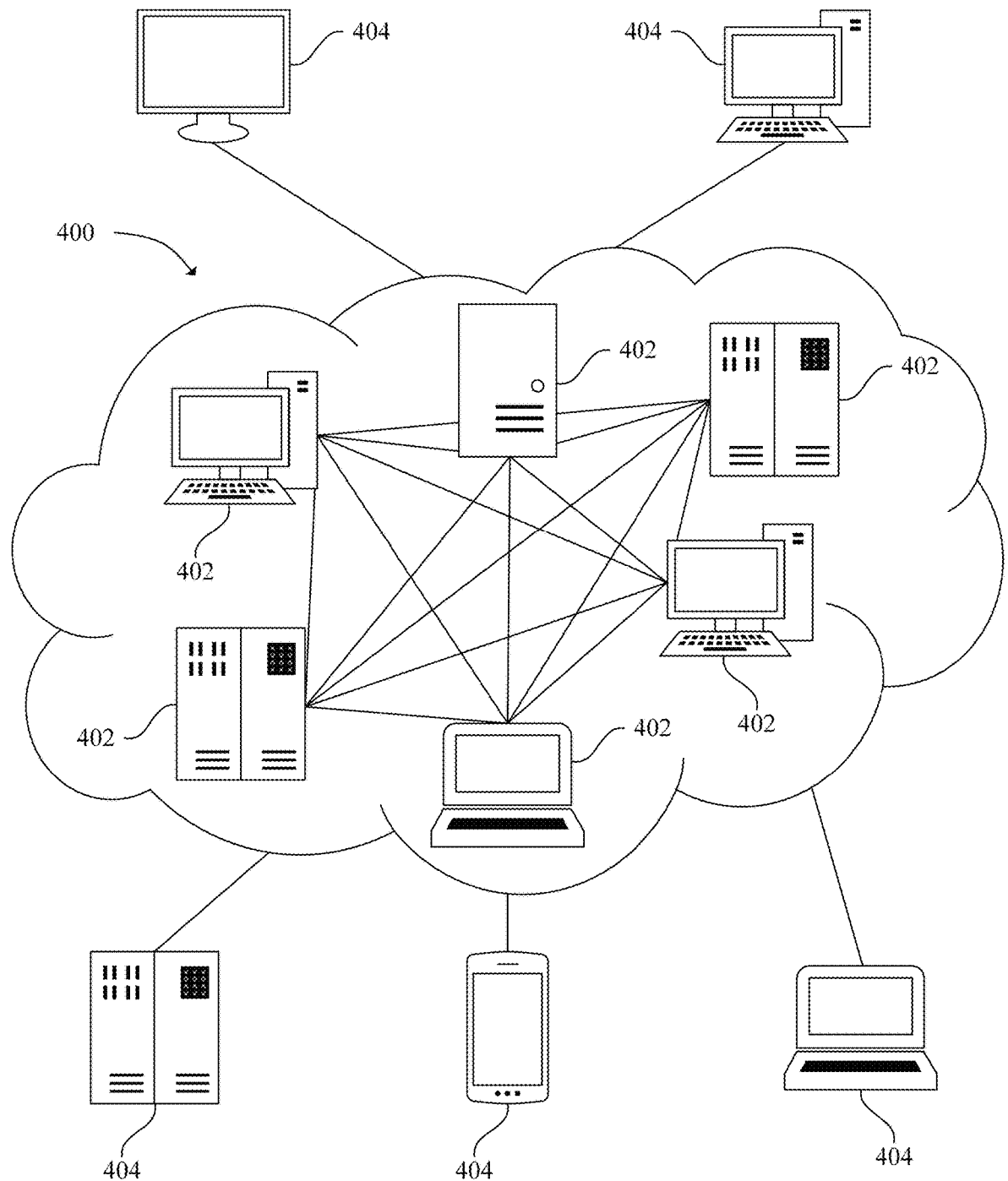
FIG. 4 depicts a cloud computing environment in accordance with an exemplary embodiment.

Briefly turning to FIG. 4, a cloud computing environment 400 is shown in accordance with an exemplary embodiment. As illustrated in FIG. 4, the cloud computing environment 400 includes one or more nodes 402. Each node 402 may include a computing device/system (i.e., a personal computer, server, a mainframe, etc.). The nodes 402 may be grouped in one or more networks and may communicate with one another. Each node 402 may include a computer readable storage medium and a processor that executes computer readable program instructions in the computer readable storage medium. As further illustrated in FIG. 4, in one embodiment, one or more devices (or systems) 404 (i.e., a personal computer, handheld device, laptop computer, server, mainframe, etc.) are connected to the cloud computing environment 400. Each device 404 may include a computer readable storage medium and a processor that executes computer readable program instructions in the computer readable storage medium. In one embodiment, a device 404 may include the computing device 132. In some embodiments, a computer readable storage medium of a node 402 or a storage medium of a device 404 may include the reconstructor 144 and/or the PACS 142. The nodes 402 or the devices 404 may be connected to a same or different network (i.e., LAN, WAN, public network, etc.) thereby allowing the nodes 402 to communication with the devices 404. In some embodiments, this connection allows the nodes 402 to provide software services to the devices 404.

Furthermore, various methods and processes (i.e., the method described below with reference to FIGS. 5 and 7) may be stored as computer readable program instructions of a system memory of a node 402 or a device 404. As such, a node 402 or a device 404 includes computer readable program instructions for monitoring and guiding patient motion during a medical image acquisition.

Figure 5:
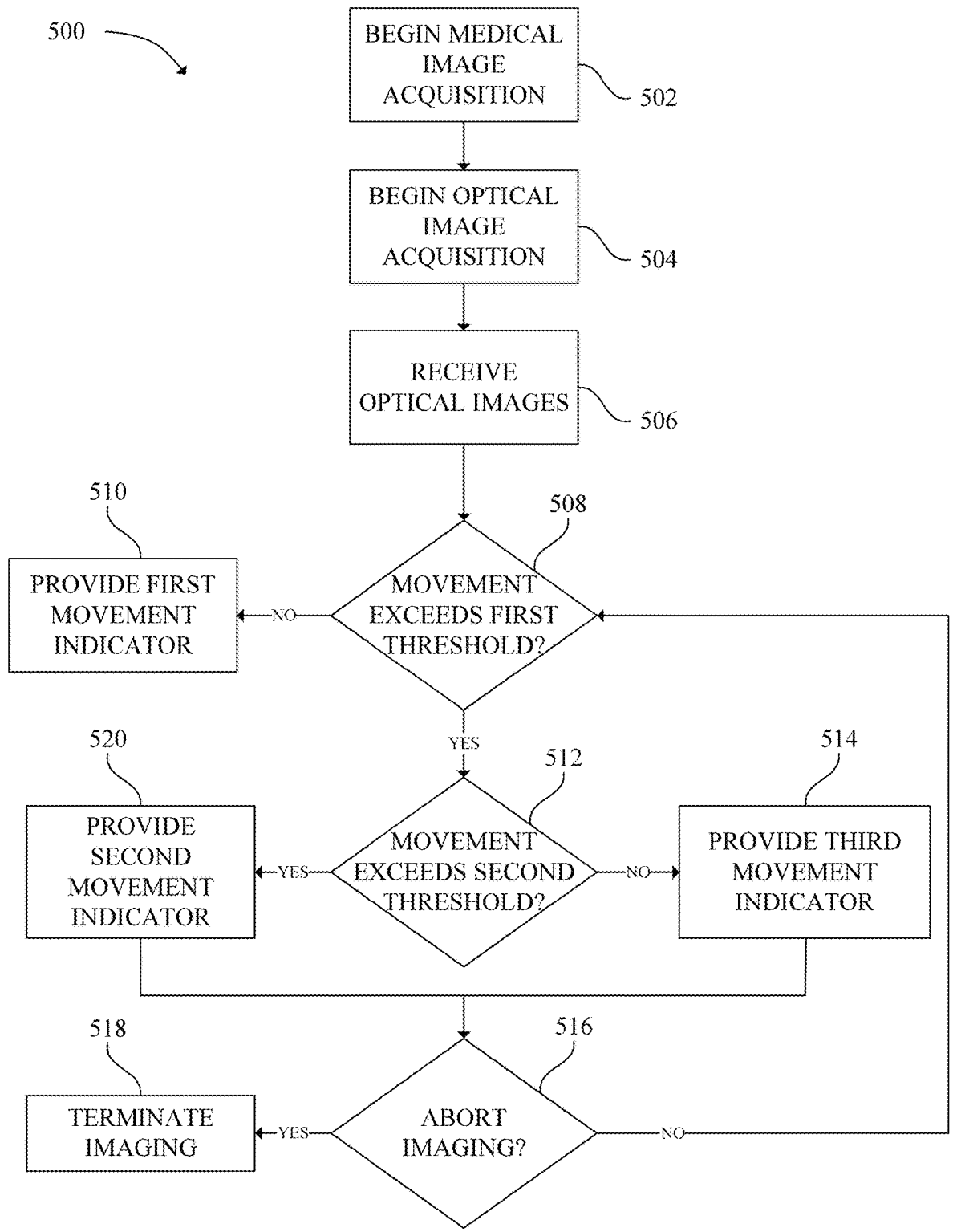
FIG. 5 is a flow chart of a method for monitoring and guiding patient motion during a medical image acquisition in accordance with an exemplary embodiment.

Referring now to FIG. 5, a flow chart of a method 500 for monitoring and guiding patient motion during a medical image acquisition is shown in accordance with an exemplary embodiment. Various aspects of the method 500 depicted in FIG. 5 may be carried out by a "configured processor." As used herein, a configured processor is a processor that is configured according to an aspect of the present disclosure. A configured processor(s) may be the processor 134, a processor of a node 402 or a processor of a device 404. A configured processor executes various computer readable program instructions to perform the steps of the method 500. The computer readable program instructions, that when executed by a configured processor, cause a configured processor to carry out the steps of the method 500 are stored in a computer readable storage medium including, but not limited to, the system memory 136, a computer readable storage medium of a node 402, or a computer readable storage medium of a device 404.

At 502, the configured processor sends a signal to begin a medical image acquisition to the control mechanism 124. In response to receiving the signal to begin a medical image acquisition, the control mechanism 124 causes the CT imaging system 100 begin acquiring a medical image of the patient 102 as previously discussed herein. In one embodiment, the configured processor sends the signal to begin a medical image acquisition in response to a user selecting an imaging protocol and/or a start icon or the like displayed in a GUI that is shown by the display 140. Furthermore, the signal to begin a medical image acquisition includes imaging parameters (i.e., X-ray source power and timing parameters, gantry rotational speed and position parameters, etc.). In response to receiving the signal to begin a medical image acquisition, the control mechanism 124 controls the rotation of the rotating gantry 106 and the operation of the X-ray source 112 based on the received parameters which causes the CT imaging system 100 to acquire a medical image of an internal region of interest (i.e., organ, tissue, etc.) of the patient 102.

In some embodiments, the signal to begin a medical image acquisition may further include a time delay. As used herein, a time delay is a period of time between when the control mechanism 124 receives the signal to begin a medical image acquisition and when the X-ray source 112 emits radiation. In one embodiment, a time delay may include a period of time after the patient 102 has been administered a contrast. While the following steps 504-520 are described as occurring during a medical image acquisition, in one embodiment, the steps 504-520 may occur during a time delay.

In one example, the patient 102 may undergo a CT scan of a kidney. In this example, the signal to being a medical image acquisition causes the CT imaging system 100 to acquire a medical image of a kidney of the patient 102. In another example, the patient 102 may undergo a CT scan of the brain with contrast. In this example, the signal to being a medical image acquisition causes the CT imaging system 100 to acquire a medical image of the brain a period of time after a contrast has been administered. This time delay may allow the contrast to reach the brain in order to properly image the brain according to an imaging protocol.

At 504, the configured processor sends a signal to begin an optical image acquisition to the camera 120. The configured processor may send the signal to begin an optical image acquisition in response to sending the signal to begin a medical image acquisition. In one embodiment, the configured processor sends the signal to begin an optical image acquisition and the signal to begin a medical image acquisition at the same time. In another embodiment, the configured processor sends the signal to begin an optical image acquisition a time after sending the signal to begin a medical image acquisition.

In response to receiving the signal to begin an optical image acquisition, the camera 120 captures optical images of an outer region of interest of the patient 102. In one embodiment, wherein the camera 120 is a video camera, the signal to begin an optical image acquisition causes the camera 120 to capture a video (i.e., a plurality of sequentially captured optical images) in real-time. The camera 120 captures the optical images at least during a medical image acquisition.

In one embodiment, the outer region of interest is a region that if moved during a medical image acquisition, may cause a motion artifact in the medical image thereby reducing the medical image quality. As such, the outer region of interest is dependent upon the internal structure to be imaged. In one example, wherein the signal to begin a medical image acquisition causes the CT imaging system 100 to acquire a medical image of the kidney, the outer region of interest includes the torso of the patient 102 as torso movement may cause a motion artifact to appear in a medical image that includes a kidney. In another embodiment, wherein the signal to begin a medical image acquisition causes the CT imaging system 100 to acquire a medical image of the brain, the outer region of interest includes the head of the patient 102 as head movement may cause a motion artifact to appear in a medical image of the brain. In yet another embodiment, wherein the signal to begin a medical image acquisition causes the CT imaging system 100 to acquire a medical image of the heart, the outer region of interest includes the chest of the patient 102 as chest movement may cause a motion artifact to appear in a medical image of the heart.

When the signal to begin a medical image acquisition includes time delay, the signal to begin an optical image acquisition may cause the camera 120 to acquire optical images during the time delay such that the camera 120 captures optical images before a medical image acquisition begins (i.e., before the X-ray source 112 begins emitting radiation). In this embodiment, the camera 120 continues to capture optical images during a medical image acquisition.

At 506, the configured processor receives optical images from the camera 120. In one embodiment, wherein the camera 120 is a video camera, the configured processor receives the optical images in the form of a real-time video.

At 508, the configured processor monitors patient movement and determines if an amount movement of the outer region of interest exceeds a first movement threshold. In one embodiment, the first movement threshold corresponds to no or little patient movement (i.e., movement that is not great enough to produce a motion artifact in a medical image). The configured processor determines if an amount of patient movement in the received optical images exceeds the first movement threshold. In one embodiment, in order to determine if an amount of patient movement exceeds the first movement threshold, the configured processor compares a most recently received image (i.e., a live image) to a previously received image. The configured processor may execute motion analysis software stored in a computer readable storage medium (i.e., the system memory 136) to process the two optical images (i.e., a live image and a previously received image) in order to track and determine an amount of movement of the outer region of interest. The motion analysis software may determine an amount of movement of the outer region of interest. For example, when the outer region of interest is the torso, and the torso moves three inches to the right in a second image when compared to a first image, the configured processor may determine the amount of movement as three inches.

The configured processor then compares the amount movement against the first movement threshold. The first movement threshold may be determined based on the internal structure to be imaged as more or less movement of the outer region of interest may be needed to cause a motion artifact with respect to different internal structures. For example, the first movement threshold may be higher (i.e., corresponding to more determined movement) with respect to the kidney than the heart as a greater amount of movement is needed to produce an image artifact in a medical image of the kidney than the heart.

At 510, in response to determining the amount of movement of the outer region of interest does not exceed the first movement threshold, the configured processor sends a first movement indicator to as at least one of the light 122 and the speaker 127 of the intercom. In response to receiving a movement indicator signal (i.e., the first movement indicator signal), the light 122 and/or the speaker 127 provides a movement indicator to the patient 102. As used herein "a movement indicator" may include an audible and/or visual indicator that notifies the patient if they are moving beyond a movement threshold. Accordingly, a movement indicator may guide patient movement as the patient may move less or continue to remain still in response to seeing and/or hearing a movement indicator. Specifically, in response to receiving the first movement indicator, the light 122 and/or the speaker 127 provides a first movement indicator to the patient 102. In response to receiving the first movement indicator, the light 122 emits a first light. For example, the first movement indicator may cause the light 122 to emit green light as the color green may visually indicate to the patient 102 that they are remaining motionless as required to obtain a high-quality medical image. Furthermore, in response to receiving the first movement indicator, the speaker 127 plays a first message (i.e., a prerecorded message). For example, the movement indicator may cause the speaker to play a first message that states "thank you for remaining still" as this notifies the patient 102 that they are remaining motionless as required to obtain a high-quality medical image.

At 512, in response to determining the amount of movement of the outer region of interest exceeds the first movement threshold, the configured processor determines if the patient 102 movement exceeds a second movement threshold. In one embodiment, the second movement threshold corresponds to an amount of movement needed to produce an image artifact that will render the medical image of the internal structure unusable for diagnostic purposes. The second movement threshold may be dependent upon the internal structure to be imaged as more or less motion of the outer region of interest may be needed to cause a motion artifact that will render a medical image of the internal structure unusable for diagnostic purposes.

At 514, in response to determining the amount of movement of the outer region of interest does not exceed the second movement threshold, the configured processor sends a second indicator to at least one of the light 122 and the speaker 127. In response to receiving the second indicator, the light 122 emits a second light. For example, the second indicator may cause the light 122 to emit yellow light as the color yellow may visually indicate to the patient 102 that they are moving, but the movement is not enough to render the medical image unusable for diagnostic purposes. In response to receiving the first movement indicator, the speaker 127 plays a second message. For example, the second movement indicator may cause the speaker to play a second message that states "you are moving, please stay still or we may have to stop the examination" as this notifies the patient 102 that they are moving.

Furthermore, at 514, the configured processor sends a first movement notification to the display 140. The first movement notification notifies a technician operating the CT imaging system 100 that the patient 102 is moving and that the movement may cause a minor motion artifact (i.e., a motion artifact that may not render the medical image unusable for diagnostic purposes). The first movement notification may further notify the technician that the movement may not render a medical image unusable for diagnostic purposes.

Figure 6:
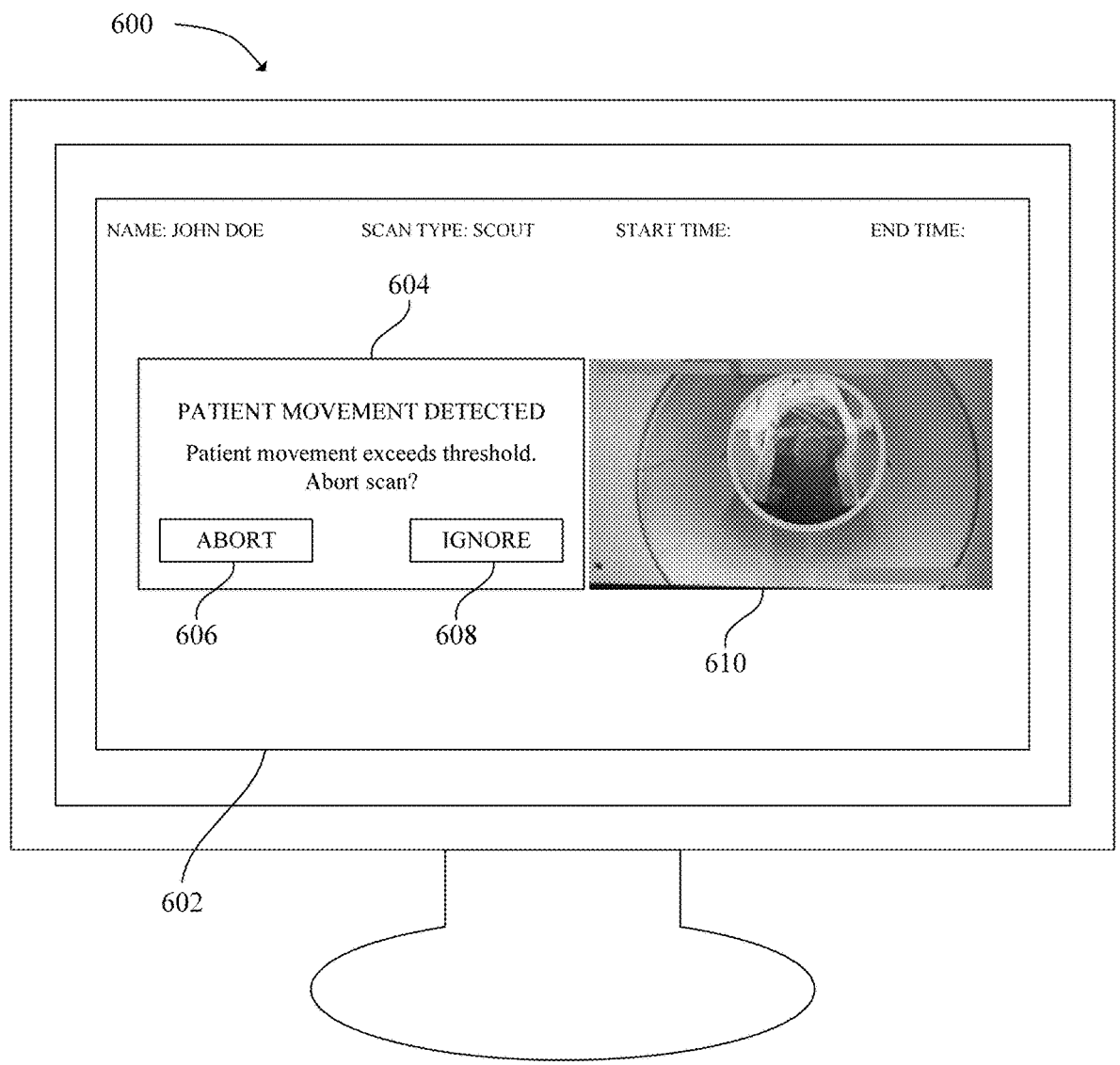
FIG. 6 depicts a graphical user interface shown by a display in accordance with an exemplary embodiment.

At 516, the configured processor determines whether to abort or proceed with a medical image acquisition. Briefly turning to FIG. 6, a display 600 with a GUI 602 that displays a first movement notification 604 is shown in accordance with an exemplary embodiment. In some embodiments, the display 600 may be the display 140. As shown in FIG. 6, the first movement notification 604 provides an abort scan icon 606 and an ignore icon 608. In some embodiments, the notification 604 may further include a viewport 610 that displays an optical image (i.e., a live image) captured by the camera 120. The configured processor determines to abort the medical image acquisition when the technician selects the abort icon 606 and determines to proceed with the medical image acquisition when the technician selects the ignore icon 608.

At 518, in response to determining to abort image acquisition, the configured processor sends an abort signal to the control mechanism 124. In response to receiving the abort signal, the control mechanism causes the X-ray source 112 to stop emitting radiation thereby ending image acquisition.

In response to determining to proceed with the medical image acquisition, the method 500 may return to 508 to determine a second patient movement and compare the determined second patient movement against the first movement threshold.

At 520, in response to determining the determined movement of the outer region of interest exceeds the second movement threshold, the configured processor sends a third movement indicator such as, at least one of the light 122 and the speaker 127. In response to reviving the third movement indicator, the light 122 emits a third light. For example, the third movement indicator may cause the light 122 to emit red light as the color red may visually indicate to the patient 102 that they are moving, and the movement may be enough to render the medical image unusable for diagnostic purposes. In response to receiving the third movement indicator signal, the speaker 127 may play a third message. For example, the third movement indicator may provide a third message that states "you are moving, please stay still, otherwise we may be forced to end this procedure" as this notifies the patient 102 that their movement may cause the medical imaging procedure to be terminated.

Furthermore, at 520, in response to determining the amount of movement exceeds the second movement threshold, the configured processor sends a second movement notification to the display 140. The second movement notification notifies a technician operating the CT imaging system 100 that the patient 102 is moving and that the movement may cause a motion artifact in the medical image. The second movement notification may further notify the technician that the movement may render a medical image unusable for diagnostic purposes.

In response to sending the third movement indicator and the second notification, the configured processor proceeds to 516 and determines whether to abort or proceed with the medical image acquisition. In one embodiment, the configured processor may automatically determine to abort the medical image acquisition in response to the amount of movement exceeding the second movement threshold. In response to automatically aborting image acquisition, the second notification indicates image acquisition was aborted due to patient 102 movement. In some embodiments, the second notification is similar to the first notification, is displayed in a GUI, includes an abort and ignore icon, and may provide a viewport that displays an optical image (i.e., a live image) captured by the camera 120. The configured processor determines to abort the medical image acquisition when the technician selects the abort icon and determines to proceed with the medical image acquisition when the technician selects the ignore icon.

In some embodiments, the first and/or second notification may include an audio message notifying the technician that the patient 102 is moving. In these embodiments, the configured processor outputs the first and/or the second notification to a speaker.

In response to determining to abort the medical image acquisition, the method 500 proceeds to 518 wherein image acquisition is terminated. In response to determining to proceed with the medical image acquisition the method 500 may return to 508 to determine a second patient movement and compare the determined second patient movement against the first movement threshold. The method 500 continues to determine patient movement at 508 and compare the patient movement against the first movement threshold at 508 and the second movement threshold at 512 until image acquisition has ended. Image acquisition ends when the X-ray source 112 stops emitting radiation.

Figure 7:
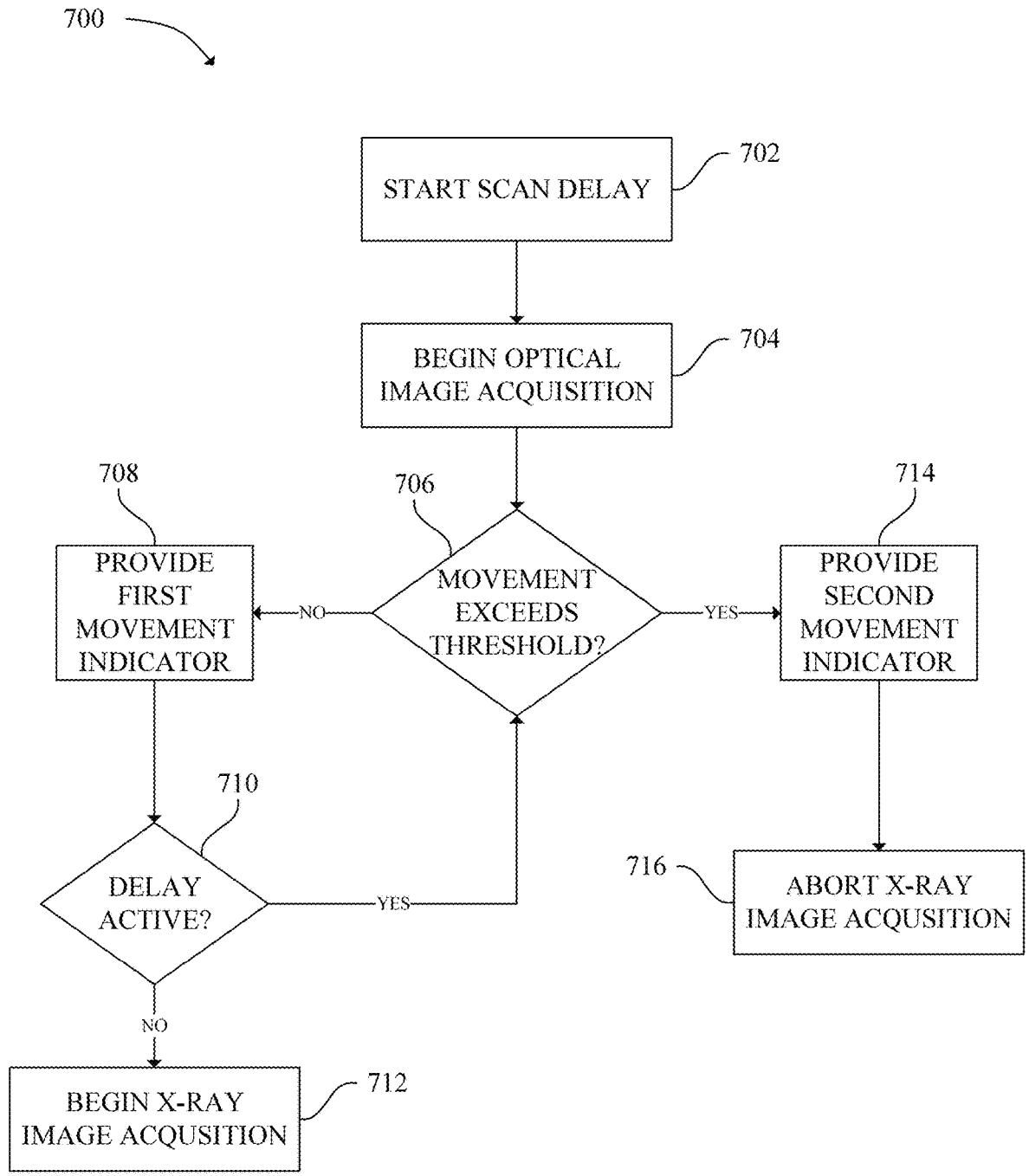
FIG. 7 is a flowchart of another method for monitoring and guiding patient motion during a medical image acquisition in accordance with an exemplary embodiment.

Referring now to FIG. 7, a flow chart of a method 700 for monitoring and guiding patient motion during a medical image acquisition is shown in accordance with an exemplary embodiment. Various aspects of the method 700 depicted in FIG. 7 may be carried out by a configured processor. A configured processor executes various computer readable program instructions to perform the steps of the method 700. The computer readable program instructions, that when executed by a configured processor, cause a configured processor to carry out the steps of the method 700 are stored in a computer readable storage medium including, but not limited to, the system memory 136, a computer readable storage medium of a node 402, or a computer readable storage medium of a device 404.

At 702, the configured processor sends a signal to begin a medical image acquisition (i.e., X-ray image acquisition) to the control mechanism 124 as previously discussed with respect to step 502. In this embodiment, the signal to begin a medical image acquisition includes a time delay and imaging parameters. In response to receiving the signal to begin a medical image acquisition, the control mechanism 124 controls the rotation of the rotating gantry 106 and the operation of the X-ray source 112.

At 704, the configured processor sends a signal to begin an optical image acquisition to the camera 120 as previously discussed with respect to 504. In response to receiving the signal to begin an optical image acquisition, the camera 120 captures optical images of an outer region of interest of the patient 102. In one embodiment, wherein the camera 120 is a video camera, the signal to begin an optical image acquisition causes the camera 120 to capture a video (i.e., a plurality of sequentially captured optical images) in real-time. The camera 120 captures the optical images at least during the time delay. In one embodiment, the outer region of interest is a region that if moved during the medical image acquisition, may cause a motion artifact in the medical image thereby reducing the medical image quality.

At 706, the configured processor monitors patient movement and determines if an amount of movement of the outer region of interest exceeds a movement threshold. The configured processor monitors and determines an amount of patient movement in optical images sent to the processor by the camera 120 as discussed with respect to 508. In one embodiment, the movement threshold corresponds to an amount of movement needed to produce an image artifact that will render the medical image of the internal structure unusable for diagnostic purposes and the movement threshold may be dependent upon the internal structure to be imaged as more or less motion of the outer region of interest may be needed to cause a motion artifact that will render a medical image of the internal structure unusable for diagnostic purposes.

At 708, in response to determining the determined amount of movement of the outer region of interest does not exceed the movement threshold, the configured processor sends a first movement indicator to at least one of the light 122 and the speaker 127. In response to receiving the first movement indicator, the light 122 and/or the speaker 127 provides a first movement indicator as previously discussed herein with respect 510.

At 710, the configured processor determines if there is time remaining in the time delay. At 712, in response to determining there is no time remaining in the time delay, the configured processor begins a medical image acquisition (i.e., begins X-ray image acquisition) as previously discussed. In response to determining there is time remaining in the time delay, the method 700 may return to 706 to continue monitoring patient movement until the time delay has ended.

At 714, in response to determining the determined amount of movement of the outer region of interest exceeds the movement threshold, the configured processor sends a second indicator to at least one of the light 122 and the speaker 127. In response to receiving the second movement indicator, the light 122 and/or the speaker 127 provides a second movement indicator. In one example, in response to receiving the second movement indicator, the light 122 may emit an orange light as the color orange may visually indicate to the patient 102 that they are moving, and the movement may be enough to render the medical image unusable for diagnostic purposes. In another example, in response to receiving the second movement indicator, the speaker 127 may play a message that states "please remain still. Your movement may cause us to stop this procedure" as this message indicates to the patient that their movement may force termination of the medical imaging procedure.

Furthermore, at 714, the configured processor sends a movement notification to the display 140. The second movement notification notifies a technician operating the CT imaging system 100 that the patient 102 is moving and that the movement may cause a motion artifact in the medical image. The movement notification may further notify the technician that the movement may render a medical image unusable for diagnostic purposes At 716, the configured processor sends an abort signal to the control mechanism 124. In some embodiments, the configured processor automatically sends the abort signal in response to determining the patient movement exceeds the movement threshold and in other embodiments, the configured based on a technician input as described with respect to 516. In response to receiving the abort signal, the control mechanism causes the X-ray source 112 to stop emitting radiation thereby ending image acquisition (i.e., thereby aborting X-ray image acquisition).

In addition to any previously indicated modification, numerous other variations and alternative arrangements may be devised by those skilled in the art without departing from the spirt and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments are meant to be illustrative only and should not be construed to be limiting in any manner.

What is claimed is:

1. A method comprising:
   acquiring at least one image of a patient with an imaging system;
   determining an amount of patient movement; and
   providing a movement indicator based on the determined amount of patient movement
   wherein an option is provided to abort an image acquisition based upon the amount of patient movement.

2. The method of claim 1, wherein the imaging system is a computed tomography (CT) imaging system.

3. The method of claim 1, wherein the movement indicator is a prerecorded audio message.

4. The method of claim 1, wherein the movement indicator includes a light emitted by the imaging system.

5. The method of claim 1, wherein the movement indicator is an alert displayed on a monitor.

6. The method of claim 1, further comprising:
   comparing the amount of patient movement to a movement threshold; and
   determining if the amount of patient movement exceeds the movement threshold.

7. The method of claim 6, further comprising:
   providing a first movement indicator if the amount of patient movement exceeds the movement threshold; and
   providing a second movement indicator if the amount of patient movement does not exceed the movement threshold.

8. The method of claim 3, wherein the movement threshold is based on a region of interest (ROI) of the patient being imaged.

9. The method of claim 6, further comprising:
   automatically aborting the image acquisition if the amount of patient movement exceeds the movement threshold.

10. The method of claim 5, further comprising:
    selecting the option on the alert to abort the image acquisition.

11. The method of claim 1, wherein the amount of patient movement is determined by at least one camera monitoring an outer (ROI) of the patient being imaged.

12. A system comprising:
    an imaging system configured to acquire at least one image of a patient;
    at least one camera configured to acquire a plurality of optical images of an outer ROI of the patient;
    at least one processor;
    at least one computer readable storage medium in communication with the at least one processor, wherein the at least one processor executes computer readable instructions stored in the at least one computer readable storage medium which cause the at least one processor to:
    determine an amount of patient movement; and
    provide a movement indicator based on the amount of patient movement;
    wherein an option is provided to abort an image acquisition based upon the amount of patient movement.

13. The system of claim 12, wherein the imaging system includes a gantry with a bore extending through the gantry, the bore creating an examination region; and wherein the movement indicator is a light configured to emit light into the examination region.

14. The system of claim 12, wherein the computer readable instructions further cause the at least one processor to:
    compare the amount of patient movement to a movement threshold; and
    provide a first movement indicator if the amount of patient movement exceeds the movement threshold; and
    provide a second movement indicator;
    wherein the second movement indicator is different from the first movement indicator;
    wherein the first movement indicator includes a light of a first color and the second movement indicator includes a light of a second color that is different from the first color.

15. The system of claim 14, wherein the first movement indicator further includes a first prerecorded message and the second movement indicator further includes a second prerecorded message that is different from the first prerecorded message.

16. The system of claim 12, wherein the computer readable instructions further cause the at least one processor to:
    compare the amount of patient movement to a first movement threshold;
    determine if the amount of patient movement exceeds the first movement threshold;
    provide a first movement indicator if the patient movement does not exceed the first movement threshold;
    compare the amount of patient movement to a second movement threshold, the second movement threshold is different from the first movement threshold; and
    determine if the amount of patient movement exceeds the second movement threshold;
    provide a second movement indicator if the patient movement exceeds the second movement threshold; and
    provide a third movement indicator if the patient movement does not exceed the second movement threshold.

17. A non-transitory computer readable storage medium with computer readable program instructions that, when executed by a processor, cause the processor to:
- determine an amount of patient movement by comparing a position of a patient in a first optical image to a position of the patient in a second optical image;
- provide a movement indicator based on the amount of patient movement, wherein the movement indicator is a light or a prerecorded audio message;
- compare the amount of patient movement to a movement threshold;
- determine if the amount of patient movement exceeds the movement threshold; and
- wherein if the amount of patient movement exceeds the movement threshold, automatically aborting the image acquisition.

18. The computer readable storage medium of claim 17, wherein the computer readable program instructions further cause the processor to:
- compare the amount of patient movement to a movement threshold;
- determine if the amount of patient movement exceeds the movement threshold;
- provide a first movement indicator if the amount of patient movement does not exceed the movement threshold; and
- provide a second movement indicator if the amount of patient movement exceeds the movement threshold, the second movement indicator is different from the first movement indicator;
- wherein the first movement indicator includes a first color light and the second movement indicator includes a different a second color light.

19. The computer readable storage medium of claim 18, wherein the first movement indicator further includes a first prerecorded message and the second movement indicator further includes a different second prerecorded message.

* * * * *